United States Patent
Stidham et al.

[11] Patent Number: 6,127,560
[45] Date of Patent: Oct. 3, 2000

[54] METHOD FOR PREPARING A LOWER ALKYL ESTER PRODUCT FROM VEGETABLE OIL

[75] Inventors: William D. Stidham, Glidden; Donald W. Seaman, Ralston; Myron F. Danzer, Glidden, all of Iowa

[73] Assignee: West Central Cooperative, Ralston, Iowa

[21] Appl. No.: 09/223,623

[22] Filed: Dec. 29, 1998

[51] Int. Cl.[7] .................................................. C11C 1/00
[52] U.S. Cl. .......................... 554/167; 554/169; 426/417
[58] Field of Search .................................. 554/167, 169; 426/417

[56] References Cited

U.S. PATENT DOCUMENTS

| | | |
|---|---|---|
| 2,271,619 | 2/1942 | Bradshaw et al. . |
| 2,360,844 | 10/1944 | Bradshaw et al. . |
| 2,383,580 | 9/1945 | Arrowsmith et al. . |
| 2,383,581 | 9/1945 | Arrowsmith et al. . |
| 2,383,596 | 9/1945 | Dreger . |
| 2,383,599 | 9/1945 | Glossop . |
| 2,383,601 | 9/1945 | Keim . |
| 2,383,614 | 9/1945 | Percy . |
| 2,383,632 | 9/1945 | Trent . |
| 2,383,633 | 9/1945 | Trent . |
| 2,494,366 | 1/1950 | Sprules . |
| 3,963,699 | 6/1976 | Rizzi et al. . |
| 4,303,590 | 12/1981 | Tanaka et al. . |
| 4,371,470 | 2/1983 | Matsukura et al. . |
| 4,668,439 | 5/1987 | Billenstein et al. . |
| 4,976,892 | 12/1990 | Jeromin et al. . |
| 5,190,868 | 3/1993 | Kokusho et al. . |
| 5,225,230 | 7/1993 | Seaman et al. . |
| 5,399,731 | 3/1995 | Wimmer . |
| 5,434,279 | 7/1995 | Wimmer . |
| 5,442,081 | 8/1995 | Behr et al. . |
| 5,520,708 | 5/1996 | Johnson et al. . |
| 5,525,126 | 6/1996 | Basu et al. . |
| 5,646,311 | 7/1997 | Hunt et al. . |

FOREIGN PATENT DOCUMENTS

| | | |
|---|---|---|
| 4 3519/89 | 4/1990 | Australia . |
| 2 148 897 | 6/1985 | United Kingdom . |
| 2 161 809 | 1/1986 | United Kingdom . |

*Primary Examiner*—Deborah D. Carr
*Attorney, Agent, or Firm*—Fay, Sharpe, Fagan, Minnich & McKee, LLP

[57] ABSTRACT

Comminuted soybeans are heated to high temperatures to condition the soybean oil contained therein. The soybean oil is extracted and filtered to remove solid fines, and then degummed and bleached. The prepared oil is introduced into a stirred reactor where lower aliphatic monohydric alcohol and an alkaline catalyst is introduced. Alcoholysis proceeds to virtual completion. A lower alkyl alcohol ester phase is separated out and washed with water to remove traces of unreacted alcohol and the alkaline catalyst.

13 Claims, 2 Drawing Sheets

METHOD FOR PREPARING A LOWER ALKYL ESTER PRODUCT FROM VEGETABLE OIL

BACKGROUND OF THE INVENTION

This invention relates to the art of preparing a lower alcohol ester from a soybean oil product. This purified lower alkyl soyate product has many uses, ranging from the use as a biodegradable solvent to a diesel fuel additive.

Since the end of World War II, soybeans have become a major agricultural commodity in the United States and in many other parts of the world. They are a major source of food and animal feed products for a world growing in population and, on the average, getting fed better. Each metric ton of soybeans typically contains around 183 kg of oil and around 800 kg of meal.

"Oilseeds: World Markets and Trade" in its March 1998 issue of the United States Department of Agriculture, Foreign Agricultural Service Circular Series shows that soybean production increased from 117.83 million metric tons in 1993/1994 to a projected 152.26 million tons for 1997/1998; soybean meal increased from 81.28 million metric tons in 1993/1994 to a projected 97.83 million tons for 1997/1998 and that soybean oil production from rose 18.25 million metric tons in 1993/1994 to 22.25 million tons for 1997/1998. With respect to the United States, The Wall Street Journal of Apr. 1, 1998 reported that planting in the U.S. is projected at 72 million acres as compared to a little over 60 million acres in 1995.

While the food and feed uses of soybean and its products consume by far the largest part of soybean production, industrial uses are significant and growing. While the percentage is small, it represents in actual terms significant commercial value. A recent (1997) publication, "Lipid Technologies and Applications", edited by Frank D. Gunstone et al., discusses non-food uses for soybeans, i.e., industrial uses, in chapters discussing detergents, as well as the use of oils and fatty acids in paints and surface coatings, lubricants and biofuels. Another publication (1995), "Practical Handbook of Soybean Processing and Utilization", edited by David R. Erickson, also discusses industrial uses emphasizing imminent growth of soybean usage in fuel additives, plastics and construction materials in a comprehensive chapter, "Industrial Uses for Soybeans" presented by Lawrence A. Johnson et al.

Alkyl esters from soybean oils are an important and growing part of the industrial applications of soybean products. Early uses of methylesters of soybean oil date back to the early 1940s and include uses as solvents and cleaning agents.

The prior art dating back to as early as the early 1940s consists of many techniques which discuss the alcoholysis of vegetable oils including soybean oils in the presence of a catalyst of either an acidic or caustic nature.

U.S. Pat. No. 2,271,619 describes a process to convert any higher fatty acid glyceride into lower alkyl esters by adding a saturated aliphatic monohydric alcohol with less than five carbon atoms in the presence of an alkali metal hydroxide of substantial anhydrous quality as a catalyst. The process is a batch process with the reactor temperature in the range from 86 to 212° F. The quantity of monohydric alcohol is not more than 1.75 equivalents of the glyceride. The catalyst quantity is 0.1 to 0.5% by weight based upon the glyceride.

Other U.S. patents improve or add-on to the process discussed above. U.S. Pat. Nos. 2,360,844; 2,383,632; 2,383,580; 2,383,581; 2,383,614; 2,383,633; 2,383,596; 2,383,599 add variations to U.S. Pat. No. 2,271,619, respectively, a) by adding acid to the process and spray drying a phase; b) by adding the step of distilling off the unreacted alcohol; c) by controlling the influence of the catalyst—one manner suggested is by adjusting pH in the range from 5 to 7; d) by applying the technology to fatty acid partial esters; e) by volatilizing the unreacted alcohol and acidifying the liquid body for better separation of esters and glycerin; f) by reworking the partially reacted glycerides by various methods; g) by adding, in addition to an aliphatic monohydric alcohol (not methyl alcohol), a dose of methyl alcohol to improve the separation of the liquid phases; and h) by adding a solvent to aid in phase separation.

Other U.S. patents propose additional novelties and improvements. U.S. Pat. Nos. 2,494,366; 2,383,601; 3,963,699; 4,303,590; 4,371,470; 4,668,439; 5,399,731; 5,434,279; and 5,525,126 are also variations, more or less, to U.S. Pat. No. 2,271,619 respectively, a) by adding a sufficient amount of acid catalyst to the alkaline catalyst; b) by again adding an acid esterification catalyst; c) by operating the process at elevated temperatures and vacuum to ambient pressure conditions; d) by adding a second alkaline catalyzed esterification step to a first one; e) again, by adding a second esterification step is and removing the lower alkyl ester by means of an adsorbent; f) by introducing the alcohol in the form of a gas; g) by letting the reaction take place at lower temperatures and by adding an acid; g) presenting an improved method for phase separation by using an acid; and h) using a catalyst which is a mixture of calcium acetate and barium acetate.

BRIEF SUMMARY OF THE INVENTION

The invention presented here relates to the production of lower alkyl esters from oil extracted from soybeans which were treated according to a method described in detail in U.S. Pat. No. 5,225,230.

In accordance with the present invention, there is provided a method for preparing high quality methylesters from soybean oil.

Soybeans are comminuted to a particle size range suitable for the physical and chemical reactions of the subsequent steps.

Next, the comminuted soybean particles are reacted to a high temperature (in the range of about 235 to 350° F.) for the purpose of conditioning the soybean oil contained therein as a precursor material for the subsequent alkali catalyzed alcoholysis reaction for producing methyl esters. The soybean oil is partially extracted from the heated comminuted soybean particles by mechanical means.

The soybean oil is filtered to remove soybean solid fines. The filtered and extracted oil is then degummed by means of phosphoric acid, water and caustic in preparation for the next step. The degummed soybean oil is bleached using either an activated clay catalyst or a natural bleaching medium such as acid-activated rice hulls. Thereafter, the prepared soybean oil is heated to the desired reaction temperature and introduced into a stirred reactor vessel.

A defined mixture of a lower aliphatic monohydric alcohol and substantially anhydrous sodium hydroxide is then introduced into the reactor vessel. The alcoholysis is allowed to proceed to virtual completion. After completion of the reaction, agitation in the reactor vessel is stopped and the heavy glycerol phase is allowed to separate from lower alkyl alcohol ester phase which is still contaminated with unreacted alcohol and the catalyst. Subsequently, the heavy glycerol phase is drained from the vessel.

The lower alkyl alcohol ester phase is washed with water to remove the traces of unreacted alcohol and the catalyst. This is most effectively done by trickling water or sparging water through the lower alkyl ester phase using a washing column of a special design. This step may be repeated several times to reach the desired level of purity of the ester phase.

A benefit of the present invention is that the high temperature step in preparing the soybean material for subsequent mechanical removal of the oil, i.e., screw pressing, results in a soybean oil which is of a higher quality than either solvent extracted soybean oil or a soybean oil prepared by the conventional full pressing, i.e., a process in which the soybean material has not been exposed to elevated temperatures.

Another benefit of the subject invention is that a soybean oil prepared in this manner has unique qualities that make the soybean oil highly suitable for subsequent conversion to lower alcohol esters including the technically and economically significant methyl esters. Specifically, the high temperature step sequesters more of the gums in the screw press cake, resulting in a soybean oil containing lower levels of gums. Moreover, the gums in the oil are substantially of the hydratable gum (hydratable phospholipid) variety. The soybean oil thus obtained has the advantage that upon water or water/acid degumming and caustic neutralization, a soybean oil is obtained that is very low in gums and therefore, lends itself to improved conversion to purer lower alkyl alcohol esters.

Yet another benefit of the present invention is that the water washing step which is performed by trickling water through or water sparging the segregated lower alcohol ester phase in a counter-current washing column of a special design, results in the production of a clean and highly purified ester product.

Still other benefits and advantages of the present invention will become apparent to those skilled in the art upon a reading and understanding of the following detailed description.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof.

DETAILED DESCRIPTION OF THE INVENTION

Figure 1:
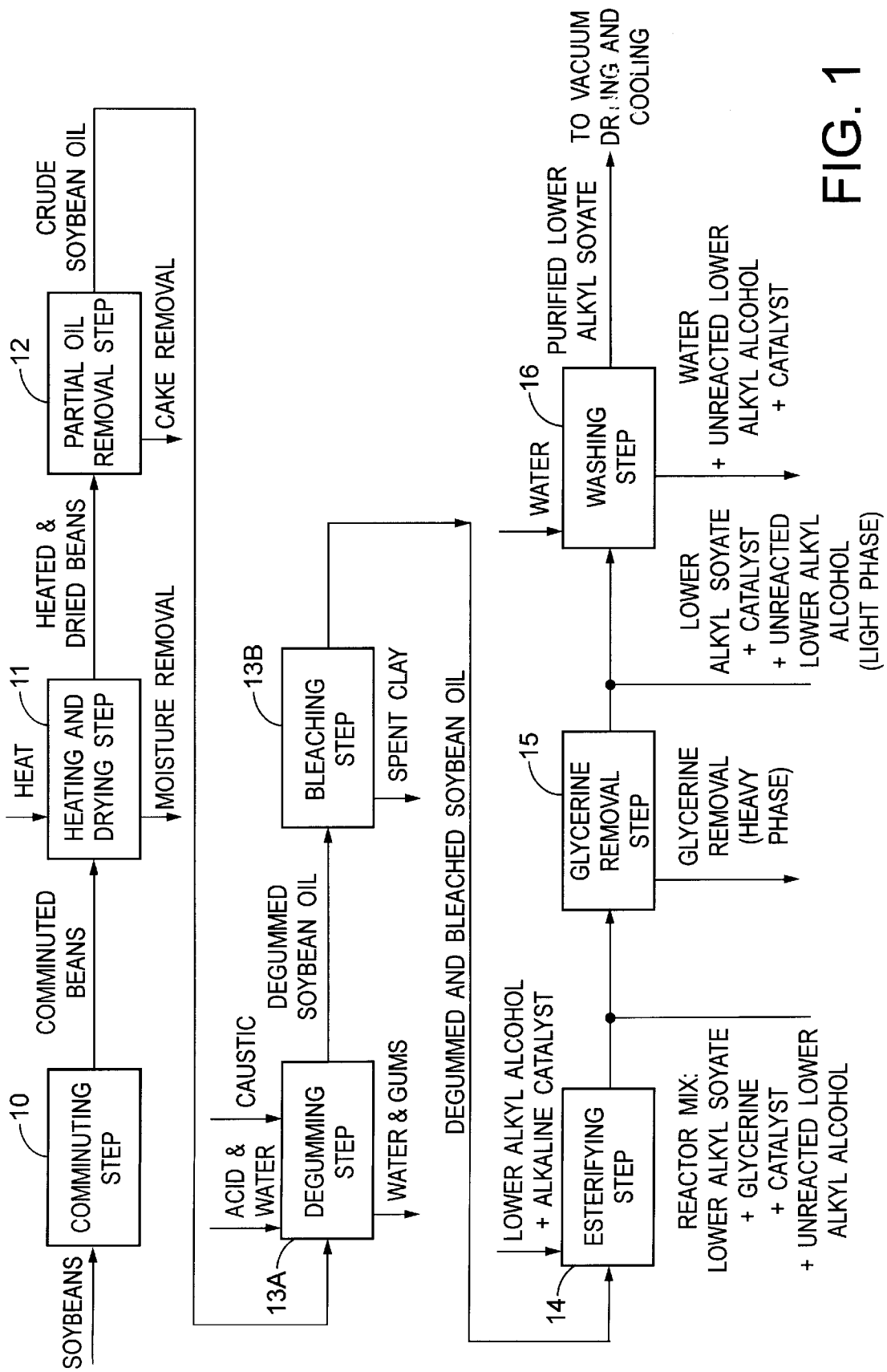
FIG. 1 is a block diagram illustrating the steps in the practice of the present invention for converting a unique soybean oil from a soybean process into a lower alkyl ester of that oil.

Referring now to the drawings wherein the showings are for purposes of illustrating the preferred embodiments of the invention only and not for the purposes of limiting same, FIG. 1 is a block diagram showing the steps followed in practicing the present invention. In particular, FIG. 1 sets forth the steps of comminuting the soybeans, heating and full pressing the soybean material to substantially remove the soybean oil therefrom, degumming the soybean oil, bleaching the oil, reacting the bleached, degummed soybean oil with a lower alcohol in the presence of a alkaline catalyst, separating the phases of reacted products, i.e., the heavy glycerol phase and the lighter lower alkyl alcohol ester phase contaminated with unspent lower alkyl alcohol and the alkaline catalyst and, as a final step, washing the lower alcohol ester product with water in a washing column to produce a clean and refined lower alcohol ester product.

A description of the relevant steps of the subject invention would include the comminuting step (block 10), the heating and drying step (block 11), the partial oil removal step (block 12), the degumming step (block 13A), the bleaching step (block 13B), the esterifying step (block 14), the phase separation or glycerine removal step (block 15) and finally the washing step (block 16).

Block 10 shows the commuting step in which soybeans from storage source are comminuted to a desired particle range. A practical range is from smaller than 200 mesh to as large as approximately one-eight of an inch in average diameter.

Block 11 in FIG. 1 represents a high-temperature heating step. At this point the comminuted soybeans are heated at elevated temperatures in the range of about 235 to 350° F., and maintained at these elevated temperatures for about 1 to 60 minutes. Since the process of heating the soybeans causes the soybeans to lose moisture, i.e. to dry, this step is referred to as a "heating and drying" step. The objective of this step, relevant to the present invention, is to condition the soybean oil for the subsequent degumming and esterifying steps.

Block 12 on FIG. 1 represents the partial removal of the soybean oil from the soybeans. This step is relevant as the production step of the conditioned oil to be processed through the subsequent steps of the present invention.

Block 13A on FIG. 1 shows the step in which the soybean oil from the previous step is filtered and subsequently degummed with water and phosphoric acid and neutralized with a caustic solution.

Block 13B on FIG. 1 sets forth a bleaching step in which the degummed oil is bleached for the purpose further removing traces of phospholipids and soaps which may have been formed in the previous step, to decompose the peroxides, to remove or change any oxidation products, and finally to reduce trace metal content. To this purpose 0.5% to 1.5% by weight of an activated absorbent such as a bentonite clay, acid leached powder, Grade F-160 (such as that available from Engelhard Corporation, Jackson, Miss.) or acid treated natural absorbents such as rice hulls is used.

Block 14 on FIG. 1 is the step in which the cleaned and degummed soybean oil is reacted with a lower alkyl alcohol in the presence of an alkaline catalyst, to produce lower alkyl alcohol esters and glycerol. The reaction takes place at 140° F. In the case of the lower alkyl alcohol being methyl alcohol, the ratio of methyl alcohol added to soybean oil is about 1 to 6.5 and the ratio of sodium hydroxide to soybean oil is about 1 to 1,000. The reaction takes up to 60 to 90 minutes to be substantially complete.

Block 15 on FIG. 1 is the glycerine removal step in which the reacted products are put in a quiescent state with time allowed for the substantial separation of the heavy glycerine phase from the lighter lower alkyl alcohol ester phase. The latter phase is contaminated with unreacted alcohol and the alkaline catalyst. The time required for the separation step is as high as sixty minutes. At the end of the separation step, the glycerine phase is separated from the product phase.

A final step represented as 16 on FIG. 1 is the washing step in which water is trickled or sparged through the lower alkyl alcohol ester product in a washing column designed for optimum contact between the two liquid phases. The washing step takes place with wash water at the same temperature as that of the lower alkyl alcohol ester products, namely about 140° F. The washing process itself is continued until the degree of purity required is achieved.

Typically, the lower alkyl alcohol ester product is dried under vacuum conditions to remove traces of wash water and cooled from 140° F. to a lower temperature suitable for storage (typically 100° F. or less).

Figure 2:
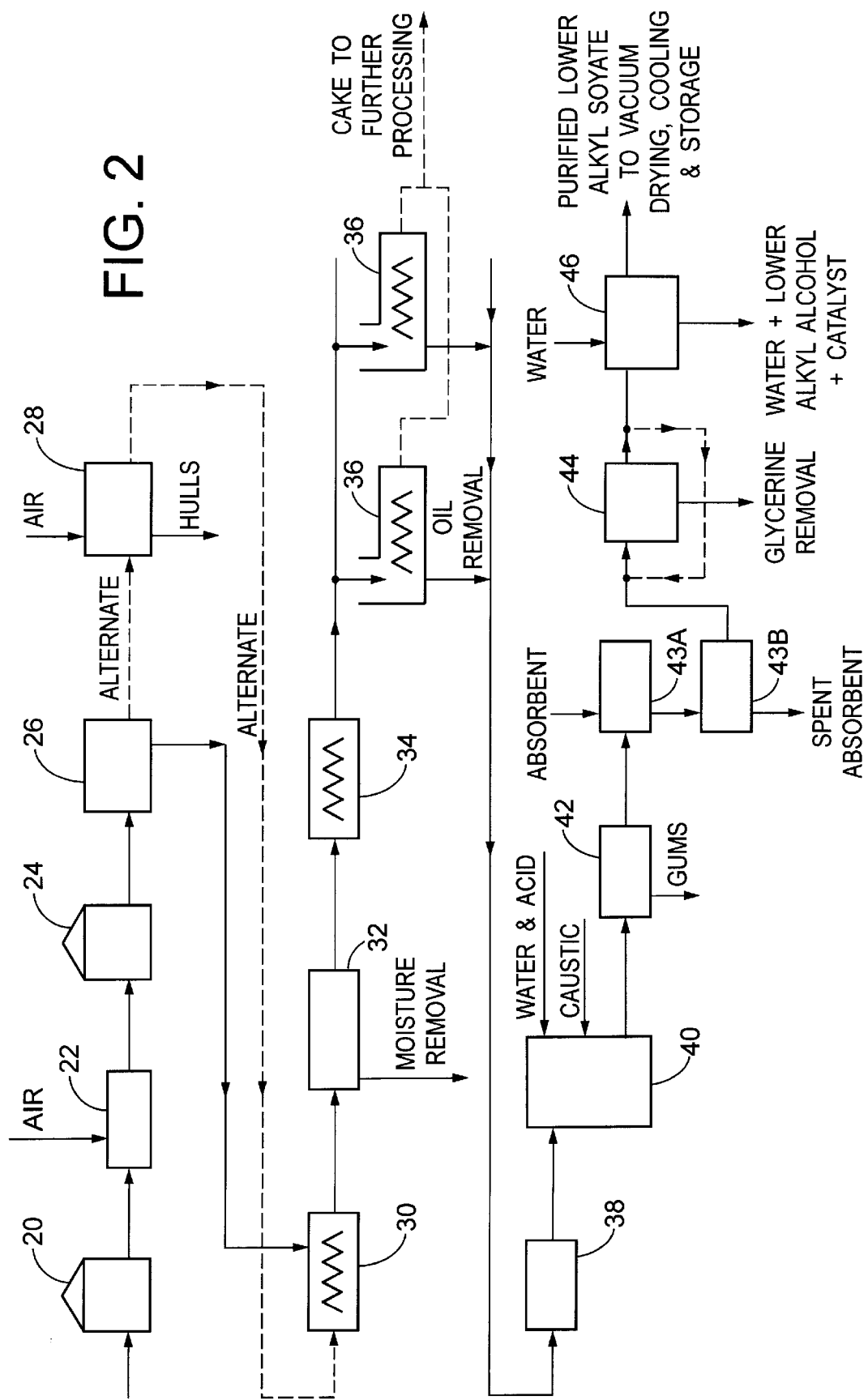
FIG. 2 is a schematic diagram of a plant constructed in accordance with the present invention for converting a unique soybean oil from a soybean extraction process into a lower alkyl ester of that oil.

Turning now to FIG. 2, a schematic representation of a plant constructed in according with the present invention is shown. Reference is made to U.S. Pat. No. 5,225,230, "Method for Preparing a High Bypass Protein Product," incorporated herein by reference, for further technical details of the steps prior to degumming the crude soybean oil. Harvested soybeans are delivered to a processing plant and directed to a receiving or holding tank 20 from where they are discharged to conveyors that conduct the soybeans to the cleaning equipment. The beans are cleaned using cleaning equipment 22. The purpose of the cleaning step is to remove dirt, twigs, and other items.

After they have been cleaned, the soybeans may be stored in a storage bin 24 and held for processing at a later date. Alternatively, the cleaned soybeans may be transmitted directly from storage bin 24 for further processing.

Next, the soybeans are transferred to comminuting equipment 26. Here, the soybeans are comminuted using equipment commonly used for these purposes and known to those skilled in the art of soybean processing. Examples of such comminuting equipment are cracking rolls and hammer mills.

An optional step may comprise dehulling of the soybeans to remove a smaller or larger portion of the hulls. If it is desired to dehull or partially dehull the soybeans, the comminuted soybeans are transferred to hull removal equipment 28 which causes air to flow through the cracked soybeans and hulls, for the purpose of dislodging and carrying away the hulls. As such, removal of the hulls may positively affect the quality parameters of the meals and it may also prevent excessive wear of the equipment for soybean oil removal, but it does not affect the subsequent processing steps leading up to converting the soybean oil into a lower alkyl alcohol ester product.

The comminuted soybeans are conducted by means of conveyor 30 to the high temperature reactor 32. The physical form of the reactor is conducive to heating and maintaining the soybean particles at a temperature range of roughly 235 to 350° F. for a period of between about 1–60 minutes in order to condition the soybean oil in the soybean particles for improved degumming and conversion into ester products in the subsequent steps of this invention. The conditioned soybean particles are conducted to the subsequent step by means of a conveyor or conveyor system 34.

A further step is to mechanically extract the comminuted and heated and conditioned soybeans particles in a screw press or bank of screw presses 36 which is also used in conventional soybean processing for this same purpose. The soybean solids containing some residual oil are further processed to prepare products unrelated to this invention.

The oil from screw press bank 36 is conducted to a filter press 38 for the purpose of removing fines, i.e., small particles of soybean solids, which are generated in the presses 36 and flow out of the presses with the soybean oil.

The soybean oil is pumped to a conditioning tank 40 in which the soybean oil is contacted with water-diluted phosporic acid under controlled stirring conditions and holding times. Caustic is added to neutralize the acid. Under these conditions a significant portion of the gums are hydrated and the gums are agglomerated. These gum agglomerations also tend to capture fines, etc. which were not removed in the previous filtering step.

Subsequently, the treated soybean oil is conducted to a degumming centrifuge 42 which removes the agglomerated gums and the contaminants captured therein.

A further step is to bleach the degummed oil in a bleaching vessel 43A and a filter press 43B.

Next, the soybean oil is pumped to a heater to bring it up to the desired reaction temperature, i.e. 140° F., and then to the reactor tank 44 in which the soybean oil is maintained in a stirred condition by continuously pumping the tank contents in and out of the tank. Subsequently, a mixture of the desired lower alkyl alcohol and the alkaline catalyst are added in the suitable proportions. For example, to prepare methyl soyate, i.e., methyl esters of the soybean oil, one part of methyl alcohol is added to each six and one half parts of soybean oil and one part of substantially anhydrous sodium hydroxide is added to each one thousand parts of soybean oil. The reaction is substantially complete in 60 to 90 minutes, after which the reactor is put in a rest mode, i.e., the agitation is stopped by means of shutting down the pump.

Subsequently, the reacted products are allowed to gravity separate in the reactor vessel 44. The time period allowed for separation is such that separation of the heavy glycerine phase and lighter ester product phase is substantially complete. For methyl soyate preparation, separation is complete in about thirty to sixty minutes. At the end of the separation, the heavy glycerine phase is drained from the bottom of the reactor vessel.

In the next step of the present invention, the lighter phase is transferred from the reactor vessel 44 to a washing column 46 of a special design. In this column 46 the ester products are washed with heated washwater (at about 140° F.) to remove the contaminants which are the unreacted portion of the lower alkyl alcohols and the alkaline catalyst. The manner in which the washing step takes place is critical to the degree of purity achieved at the end of the washing step. Water is trickled very slowly through the lighter ester phase. The heavier spent water phase is collected with the alcohol and alkaline catalyst contained therein at the bottom of the wash column and removed by draining. Also, this step washes out quantities of soaps produced by the reaction of the free fatty acids in the lighter phase with the alkaline catalyst, if the nature of the catalyst is such that it can react with the free fatty acids. Suitable catalysts for this process include sodium hydroxide or potassium hydroxide. This washing step is continued until the desired purity is achieved. The ratio of wash water to soybean oil is about one half to one part of water to one part of soybean oil.

Subsequent steps are typical for any vegetable oil derived product. The lower alkyl alcohol ester products are vacuum dried to remove traces of moisture and subsequently cooled to a desired storage temperature.

EXAMPLE

A methyl soyate production plant was added to an existing facility for comminuting, heating and mechanically extracting soybeans in accordance with the techniques of this invention.

Raw soybeans were fed to the plant at roughly 800 tons per day.

The comminuted soybeans were fed to an indirectly steam-heated rotary dryer which was operated in a manner to produce soybean particles which were heated over a period of roughly 20 minutes (plus or minus 2 minutes) to a temperature of 290° F. (plus or minus 5° F.). The soybean particles were discharged from the kiln at roughly 2 to 3% final moisture.

The heated soybeans from the kiln were conducted to a bank of eighteen Dupps 10 Pressor screw presses with specially modified shafts operating in parallel. Each press produced roughly 6 tons of crude soybean oil per day and 35 tons of cake. As cake discharge temperatures from the screw presses are typically about 280 to 321° F., it was realistic to assume that the soybean oil had also been exposed to the same temperatures.

The crude soybean oil from the presses was filtered in a filter press to remove fines and then stored in a storage tank. Later, the oil was heated and fed to a conditioning vessel in which dilute phosphoric acid and dilute caustic was added to the soybean oil. The mixture was then stirred under conditions of low shear for a determined length of time sufficient to allow for the hydrated gums to agglomerate. The quantity of caustic used was determined by the need to neutralize the acid. Subsequently, the conditioned soybean oil was fed to a Westfalia disc centrifuge for substantially complete removal of the gums. All of these steps are known to those skilled in the art of degumming soybean oil.

The degummed oil was stored in a storage tank. Whenever inventory of methyl soyate required additional production of same, batch quantities of degummed soybean oil were heated to 140° F. The process used was a batch process which required a batch of 1,150 gallons (8,625 lbs.) of degummed soybean oil.

The catalyst was prepared in a catalyst mix tank by thoroughly mixing 202 gallons (1,133 lbs.) of methanol with 85 lbs. of sodium hydroxide. In relationship to the quantity of soybean oil, the quantity of methanol was 1/6.5 and the quantity of sodium hydroxide was 1/1,000. The catalyst/methanol mixture was also heated to 140° F.

The batch of soybean oil and the batch of catalyst/methanol mixture were one by one introduced into a reactor vessel wherein the liquids were kept under constant stirring conditions by means of pumping the mixture continuously in and out of the vessel. Mixing took place for a period of 60 minutes. At the end of the 60 minutes, agitation was ceased by stopping the pump. The mixture was allowed to segregate into two phases: 1) a heavy glycerine phase which would settle at the bottom of the reactor tank, and 2) a lighter methyl soyate phase contaminated with unreacted methanol and the sodium hydroxide catalyst.

The heavy phase, i.e. the glycerine was drained from the bottom of the reactor vessel to be purified and stored.

The lighter phase, i.e. the methyl soyate with the unreacted methanol and the sodium hydroxide catalyst, was subsequently introduced into a counter current washing column of a special design. This lighter phase was at 140° F. Five hundred gallon batches of wash water were prepared by heating to 140° F.

The wash column used is 12" in diameter and 24 ft. high. The methyl soyate phase is pumped in the bottom of the column and removed near the top. The methyl soyate flow rate is approximately 3 to 8 GPM. Wash water is introduced through a spray bar near the top of the column and the water with the contaminants, i.e., unreacted methyl alcohol and catalyst drains from a drain at the bottom of the wash column. Wash water flow rate is 3 to 10 GPM. The washing process is maintained for a period of up to sixty minutes.

After completing the washing steps the methyl soyate was dried in a vacuum dryer to remove moisture traces. In this drying step the methyl soyate is heated to 190° F. and then introduced into a vacuum tank, i.e. the vacuum dryer in which a vacuum of 28 inches of mercury is maintained.

Subsequent to the drying step the methyl soyate is cooled from 190° F. to 100° F. or less for storage purposes.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

We claim:

1. A method for preparing lower alkyl esters of soybean oil fatty acids by an alcoholysis reaction of the soybean fatty acid triglycerides with a lower alcohol which comprises the successive steps of:

a) comminuting the raw soybeans to crack open their hulls and shatter their kernels;

b) heating the comminuted soybeans in a high-temperature reactor to elevated temperatures in the range of 235 to 350° F.;

c) maintaining the soybeans at the elevated temperatures for a period of 1 to 60 minutes;

d) partially removing the oil contained in the soybeans by mechanical means;

e) degumming the crude soybean oil to reduce the concentration of phospholipid in the oil;

f) bleaching the degummed soybean oil to further reduce gums and improve color of the oil;

g) esterifying the fatty acid glycerides of the soybean oil by an alcoholysis reaction with a lower alcohol in the presence of an alkali catalyst to form fatty acid alcohol esters and glycerine, the conversion of the fatty acid glyceride being in the range of 90 to 99.5% h) separating the glycerine from the crude fatty acid esterification products by settling or other mechanical means;

i) washing, in one or more steps, the crude fatty acid esterification products by trickling water through the products and allowing the mix of water and fatty acid esterification products to separate into two phases, washed and purified fatty acid esterification product and a water phase containing water, contaminants such as glycerine and unreacted lower alcohol and impurities from the soybean oil used.

2. A method for preparing lower alkyl fatty acid esters from soybean oil according to claim 1 in which the lower alcohol is methyl alcohol.

3. A method for preparing lower alkyl fatty acid esters from soybean oil according to claim 1 in which the alkali catalyst is substantially anhydrous sodium hydroxide.

4. A method for preparing lower alkyl fatty acid esters from soybean oil according to claim 1 in which the alcoholysis reaction in the reactor takes place at temperatures in the range of 140 to 200° F.

5. A method for preparing lower alkyl fatty acid esters from soybean oil according to claim 1 in which the glycerine produced is purified by coalescing the dispersed alkyl fatty acid ester-alkyl alcohol phase into a continuous phase by means of a coalescing filter.

6. A method for preparing lower alkyl fatty acid esters from soybean oil according to claim 1 in which the methyl soyate product is washed in a counter-current washing column in which the methyl soyate product and the wash water in the form of droplets move in a counter-current fashion.

7. A method for preparing lower alkyl esters of soybean oil fatty acids using an alcoholysis reaction of the soybean oil fatty acid glycerides with a lower alcohol which comprises the successive steps of:
  a) esterifying the fatty acid glycerides of the soybean oil by an alcoholysis reaction with a lower alcohol in the presence of an alkali catalyst to form fatty acid alcohol esters and glycerine, the conversion of the fatty acid glyceride being in the range of 90 to 99.5%;
  b) separating the glycerine from the crude fatty acid esterification products by settling or other mechanical means;
  c) washing, in one or more steps, the crude fatty acid esterification products by trickling water through the products and allowing the mix of water and fatty acid esterification products to separate into two phases, washed and purified fatty acid esterification product and a water phase containing water, contaminants such as glycerine and unreacted lower alcohol and impurities from the soybean oil used.

8. A method for producing lower alkyl esters of soy bean oil fatty acids according to claim 7 in which the lower alcohol is methyl alcohol.

9. A method for producing lower alkyl esters of soybean oil fatty acids according to claim 7 in which the alkaline catalyst is substantially anhydrous sodium hydroxide.

10. A method for producing lower alkyl esters of soybean oil fatty acids according to claim 7 in which the alcoholysis reaction in the reactor takes place at temperatures in the range of 140 to 200° F.

11. A method for preparing lower alkyl fatty acid esters from soybean oil according to claim 7 in which the glycerine produced is purified by coalescing the dispersed alkyl fatty acid ester-lower alkyl alcohol phase into a continuous phase by means of a coalescing filter.

12. A method for preparing lower alkyl fatty acid esters from soybean oil according to claim 7 in which the methyl soyate produced is washed in a counter current washing column in which the methyl soyate product and the wash water in the form of droplets flow in a counter current fashion.

13. A method for preparing lower alkyl esters of soybean oil fatty acids, comprising the step of:
  heating comminuted soybeans to a temperature of at least 235° F. for up to 60 minutes to condition soybean oil contained therein;
  mechanically removing soybean oil from the soybean;
  esterifying the fatty acid glycerides of the soybean oil by an alcoholysis reaction with a lower alcohol in the presence of an alkali catalyst to form fatty acid alcohol esters and glycerine;
  separating the glycerine from the fatty acid alcohol esters;
  trickling water through the fatty acid alcohol esters; and
  separating washed and purified fatty acid alcohol ester from a water phase containing water, contaminants and impurities.

* * * * *